US012723066B2

(12) United States Patent
Li et al.

(10) Patent No.: US 12,723,066 B2
(45) Date of Patent: Sep. 1, 2026

(54) SHEEP PDGFD, NUCLEIC ACIDS ENCODING PDGFD AND RECOMBINANT LENTIVIRUS, HOST CELL AND USE THEREOF

(71) Applicant: Institute of Biotechnology, Xinjiang Academy of Animal Science (China-Australia Sheep Research Centre, Xinjiang Academy of Animal Science), Urumqi (CN)

(72) Inventors: Zhonghui Li, Urumqi (CN); Wenrong Li, Urumqi (CN); Jinrui Liu, Urumqi (CN); Chenxi Liu, Urumqi (CN); Meiyu Qiu, Urumqi (CN); Yila Ma, Urumqi (CN)

(73) Assignee: Institute of Biotechnology, Xinjiang Academy of Animal Science (China-Australia Sheep Research Centre, Xinjiang Academy of Animal Science), Urumqi (CN)

( * ) Notice: Subject to any disclaimer, the term of this patent is extended or adjusted under 35 U.S.C. 154(b) by 516 days.

(21) Appl. No.: 18/322,738

(22) Filed: May 24, 2023

(65) Prior Publication Data

US 2023/0382965 A1 Nov. 30, 2023

(30) Foreign Application Priority Data

May 31, 2022 (CN) ......................... 202210606481.5

(51) Int. Cl.
*C07K 14/49* (2006.01)
*C12N 15/86* (2006.01)

(52) U.S. Cl.
CPC .............. *C07K 14/49* (2013.01); *C12N 15/86* (2013.01); *C12N 2740/15043* (2013.01)

(58) Field of Classification Search
CPC .. C07K 14/49; C12N 15/86; C12N 2800/107; A61K 38/00
See application file for complete search history.

(56) References Cited

PUBLICATIONS

Qing Li et al., Verification and Analysis of Sheep Tail Type-Associated PDGF-D Gene Polymorphisms. Animals 2020, 10, 89. Published Jan. 6, 2020. (Year: 2020).*

Xin Li et al., Whole-genome resequencing of wild and domestic sheep identifies genes associated with morphological and agronomic traits. Nature Communications (2020)11:2815. Published Jun. 4, 2020 (Year: 2020).*

Archibald et al., The sheep genome reference sequence: a work in progress. International Foundation for Animal Genetics, 41, 449-453. Published Jun. 22, 2010. (Year: 2010).*

Artemenko et al., Anti-Adipogenic Effect of PDGF Is Reversed by PKC Inhibition. Journal of Cellular Physiology 204: 646-653 (2005). Published Aug. 2005 (Year: 2005).*

Liu et al., Highly Efficient Generation of Transgenic Sheep by Lentivirus Accompanying the Alteration of Methylation Status. PLoS One 8(1). Published Jan. 29, 2013 (Year: 2013).*

GeneBank Reference Sequence XP_004016014.1, "Platelet-derived growth factor D isoform X2 [Ovis aries]", (Jul. 2021).

GeneBank Reference Sequence XP_004016015.1, "Platelet-derived growth factor D isoform X3 [Ovis aries]", (Jul. 2021).

Venkatesan et al., "Recombinant production of growth factors for application in cell culture", bioRxiv doi:10.1101/2022.02.15.480596, (Feb. 2022).

Office Action issue for the Chinese Application No. 202210606481.5 issued on Jul. 19, 2023 p. 1-6. (English translation provided).

* cited by examiner

*Primary Examiner* — Laura Schuberg
*Assistant Examiner* — Nicholas A Humphries
(74) *Attorney, Agent, or Firm* — McDonnell Boehnen Hulbert & Berghoff LLP

(57) ABSTRACT

Disclosed is a sheep PDGFD, nucleic acids encoding PDGFD and recombinant lentivirus, host cell and use thereof, which relate to the technical field of molecular cell biology. The sheep platelet-derived growth factor PDGFD includes one or two of PDGFD-T1 and PDGFD-T2. The amino acid sequence of PDGFD-T1 is set forth in SEQ ID NO:1, and the amino acid sequence of PDGFD-T2 is set forth in SEQ ID NO:2. PDGFD-T1 and PDGFD-T2 are able to significantly inhibit the differentiation and maturation of precursor adipocytes and significantly reduce the mRNA relative expression levels of adipogenic differentiation-related genes CEBPα, PPARγ, FAS, FABP4 and LPL, thereby inhibiting animal fat deposition and improving animal meat quality, and have important guiding significance in the fields of life science, medical science, animal husbandry and the like.

6 Claims, 4 Drawing Sheets

Specification includes a Sequence Listing.

PDGFD-T1

PDGFD-T2

PDGFD-T3

SEQUENCE LISTING

```
Sequence total quantity: 18
SEQ ID NO: 1            moltype = AA  length = 370
FEATURE                 Location/Qualifiers
source                  1..370
                        mol_type = protein
                        organism = synthetic construct
SEQUENCE: 1
MHRLILVYTL VCANFCSYRD TSATPQSASI KALRNANLRR DESNHLTDLY RRDETIQVTG  60
HGHVQSPRFP NSYPRNLLLT WRLHSQEKTR IQLAFDNQFG LEEAENDICR YDFVEVEDIS  120
ETSTVIRGRW CGHKEVPPRI TSRTNQIKIT FKSDDYFVAK PGFKIYYSFV EDFQPAAASE  180
TNWESVTSSI SGVSYHSPSV TDPTLTADAL DKTIAEFDTV EELLKHFNPE SWQDDLENLY  240
LDTPHHRGRS YHDRKSKVDL DRLNDDVKRY SCTPRNYSVN LREELKLTNV VFFPRCLLVQ  300
RCGGNCGCGT VNWKSCACNS GKTVKKYHEV LKFEPGHFKR RGRAKHMALV DIQLDHHERC  360
```

```
DCICSSRPPR                                                       370

SEQ ID NO: 2             moltype = AA  length = 364
FEATURE                  Location/Qualifiers
source                   1..364
                         mol_type = protein
                         organism = synthetic construct
SEQUENCE: 2
MHRLILVYTL VCANFCSYRD TSATPQSASI KALRNANLRR DDLYRRDETI QVTGHGHVQS  60
PRFPNSYPRN LLLTWRLHSQ EKTRIQLAFD NQFGLEEAEN DICRYDFVEV EDISETSTVI  120
RGRWCGHKEV PPRITSRTNQ IKITFKSDDY FVAKPGFKIY YSFVEDFQPA AASETNWESV  180
TSSISGVSYH SPSVTDPTLT ADALDKTIAE FDTVEELLKH FNPESWQDDL ENLYLDTPHH  240
RGRSYHDRKS KVDLDRLNDD VKRYSCTPRN YSVNLREELK LTNVVFFPRC LLVQRCGGNC  300
GCGTVNWKSC ACNSGKTVKK YHEVLKFEPG HFKRRGRAKH MALVDIQLDH HERCDCICSS  360
RPPR                                                             364

SEQ ID NO: 3             moltype = DNA  length = 1113
FEATURE                  Location/Qualifiers
source                   1..1113
                         mol_type = other DNA
                         organism = synthetic construct
SEQUENCE: 3
atgcaccggc tcatccttgt ctacacgcta gtctgcgcaa acttttgcag ctaccgggac  60
acctctgcca ccccgcagag cgcatctatc aaagctttgc gtaacgccaa cctcaggcga  120
gatgagagca atcacctcac agacttgtac cgaagagacg agaccatcca ggtgacagga  180
cacggccacg tgcagagtcc ccgcttccca aacagctacc ctcgcaacct gcttctgacc  240
tggcggctcc actcccagga gaaaacaagg atacagctag cctttgacaa tcagtttgga  300
ttagaggaag cggaaaatga tatctgtagg tatgattttg tagaagttga agacatatct  360
gaaaccagta ctgttattag aggacgatgg tgtggacaca aggaagttcc tccaaggata  420
acatcaagaa caaaccagat taaaataacg ttcaagtctg atgactactt tgtggctaaa  480
cctggattca agatttatta ttcttttgtg gaagatttcc aacctgcagc agcctcagag  540
accaactggg agtcagtcac aagctctatc tcaggggtat cctatcactc tccatcagta  600
acggacccca ctctcactgc ggatgctctg gacaaaacga ttgcagaatt tgatactgtg  660
gaagagctgc tcaagcactt caatcccgaa tcatggcaag acgatcttga gaatctgtat  720
ttggataccc ctcatcatcg aggcagatcg tatcatgaca ggaagtcaaa agttgacctg  780
gacaggctca acgatgatgt caagcgttac agttgcactc ccaggaatta ctccgtcaac  840
ttgagagaag agctgaagct taccaatgtg gtcttctttc cacgctgcct ccttgtgcag  900
cgctgcggag gaaactgtgg ctgtggaact gtcaactgga agtcctgtgc gtgcaattca  960
gggaaaactg tgaaaaagta tcacgaggtg ttaaagtttg aacctggcca tttcaagagg  1020
aggggcagag cgaagcacat ggctctcgtt gacatccagt tggatcatca tgagcggtgc  1080
gactgtatct gcagctcaag accacctcga taa                             1113

SEQ ID NO: 4             moltype = DNA  length = 1095
FEATURE                  Location/Qualifiers
source                   1..1095
                         mol_type = other DNA
                         organism = synthetic construct
SEQUENCE: 4
atgcaccggc tcatccttgt ctacacgcta gtctgcgcaa acttttgcag ctaccgggac  60
acctctgcca ccccgcagag cgcatctatc aaagctttgc gtaacgccaa cctcaggcga  120
gatgacttgt accgaagaga cgagaccatc caggtgacag gacacggcca cgtgcagagt  180
ccccgcttcc caaacagcta ccctcgcaac ctgcttctga cctggcggct ccactcccag  240
gagaaaacaa ggatacagct agcctttgac aatcagtttg gattagagga agcggaaaat  300
gatatctgta ggtatgattt tgtagaagtt gaagacatat ctgaaaccag tactgttatt  360
agaggacgat ggtgtggaca caaggaagtt cctccaagga taacatcaag aacaaaccag  420
attaaaataa cgttcaagtc tgatgactac tttgtggcta aacctggatt caagatttat  480
tattcttttg tggaagattt ccaacctgca gcagcctcag agaccaactg ggagtcagtc  540
acaagctcta tctcaggggt atcctatcac tctccatcag taacggaccc cactctcact  600
gcggatgctc tggacaaaac gattgcagaa tttgatactg tggaagagct gctcaagcac  660
ttcaatcccg aatcatggca agacgatctt gagaatctgt atttggatac ccctcatcat  720
cgaggcagat cgtatcatga caggaagtca aaagttgacc tggacaggct caacgatgat  780
gtcaagcgtt acagttgcac tcccaggaat tactccgtca acttgagaga agagctgaag  840
cttaccaatg tggtcttctt tccacgctgc ctccttgtgc agcgctgcgg aggaaactgt  900
ggctgtggaa ctgtcaactg gaagtcctgt gcgtgcaatt cagggaaaac tgtgaaaaag  960
tatcacgagg tgttaaagtt tgaacctggc catttcaaga ggaggggcag agcgaagcac  1020
atggctctcg ttgacatcca gttggatcat catgagcggt gcgactgtat ctgcagctca  1080
agaccacctc gataa                                                 1095

SEQ ID NO: 5             moltype = DNA  length = 38
FEATURE                  Location/Qualifiers
source                   1..38
                         mol_type = other DNA
                         organism = synthetic construct
SEQUENCE: 5
cgggatccgc caccatgcac cggctcatcc ttgtctac                        38

SEQ ID NO: 6             moltype = DNA  length = 58
FEATURE                  Location/Qualifiers
source                   1..58
```

```
                        mol_type = other DNA
                        organism = synthetic construct
SEQUENCE: 6
ccctcgagtt aagcgtagtc tgggacgtcg tatgggtatc gaggtggtct tgagctgc    58

SEQ ID NO: 7            moltype = AA  length = 191
FEATURE                 Location/Qualifiers
source                  1..191
                        mol_type = protein
                        organism = synthetic construct
SEQUENCE: 7
MHRLILVYTL VCANFCSYRD TSATPQSASI KALRNANLRR DESNHLTDLY RRDETIQVTG  60
HGHVQSPRFP NSYPRNLLLT WRLHSQEKTR IQLAFDNQFG LEEAENDICR YDFVEVEDIS  120
ETSTVIRGRW CGHKEVPPRI TSRTNQIKIT FKSDDYFVAK PGFKIYYSFV EDFQPAAASE  180
TNWESVTSSI S                                                       191

SEQ ID NO: 8            moltype = DNA  length = 1088
FEATURE                 Location/Qualifiers
source                  1..1088
                        mol_type = other DNA
                        organism = synthetic construct
SEQUENCE: 8
atgcaccggc tcatccttgt ctacacgcta gtctgcgcaa acttttgcag ctaccgggac  60
acctctgcca ccccgcagag cgcatctatc aaagctttgc gtaacgccaa cctcaggcga  120
gatgagagca atcacctcac agacttgtac cgaagagacg agaccatcca ggtgacagga  180
cacggccacg tgcagagtcc ccgcttccca aacagctacc ctcgcaacct gcttctgacc  240
tggcggctcc actcccagga gaaaacaagg atacagctag cctttgacaa tcagtttgga  300
ttagaggaag cggaaaatga tatctgtagg tatgattttg tagaagttga agacatatct  360
gaaaccagta ctgttattag aggacgatgg tgtggacaca aggaagttcc tccaaggata  420
acatcaagaa caaaccagat taaaataacg ttcaagtctg atgactactt tgtggctaaa  480
cctggattca agatttatta ttcttttgtg gaagatttcc aacctgcagc agcctcagag  540
accaactggg agtcagtcac aagctctatc tcataacgga ccccactctc actgcggatg  600
ctctggacaa aacgattgca gaatttgata ctgtggaaga gctgctcaag cacttcaatc  660
ccgaatcatg gcaagacgat cttgagaatc tgtatttgga taccccctcat catcgaggca  720
gatcgtatca tgacaggaag tcaaaagttg acctggacag gctcaacgat gatgtcaagc  780
gttacagttg cactcccagg aattactccg tcaacttgag agaagagctg aagcttacca  840
atgtggtctt ctttccacgc tgcctccttg tgcagcgctg cggaggaaac tgtggctgtg  900
gaactgtcaa ctggaagtcc tgtgcgtgca attcagggaa aactgtgaaa aagtatcacg  960
aggtgttaaa gtttgaacct ggccatttca agaggagggg cagagcgaag cacatggctc  1020
tcgttgacat ccagttggat catcatgagc ggtgcgactg tatctgcagc tcaagaccac  1080
ctcgataa                                                           1088

SEQ ID NO: 9            moltype = DNA  length = 22
FEATURE                 Location/Qualifiers
source                  1..22
                        mol_type = other DNA
                        organism = synthetic construct
SEQUENCE: 9
ccaagaagtc ggtggacaag aa                                           22

SEQ ID NO: 10           moltype = DNA  length = 21
FEATURE                 Location/Qualifiers
source                  1..21
                        mol_type = other DNA
                        organism = synthetic construct
SEQUENCE: 10
cggtcattgt cactggtcaa c                                            21

SEQ ID NO: 11           moltype = DNA  length = 21
FEATURE                 Location/Qualifiers
source                  1..21
                        mol_type = other DNA
                        organism = synthetic construct
SEQUENCE: 11
gtgccagttt cgatccgtag a                                            21

SEQ ID NO: 12           moltype = DNA  length = 20
FEATURE                 Location/Qualifiers
source                  1..20
                        mol_type = other DNA
                        organism = synthetic construct
SEQUENCE: 12
ggccagcatc gtgtagatga                                              20

SEQ ID NO: 13           moltype = DNA  length = 21
FEATURE                 Location/Qualifiers
source                  1..21
                        mol_type = other DNA
                        organism = synthetic construct
```

-continued

```
SEQUENCE: 13
ggaggtggtg atagccggta t                                            21

SEQ ID NO: 14          moltype = DNA  length = 21
FEATURE                Location/Qualifiers
source                 1..21
                       mol_type = other DNA
                       organism = synthetic construct
SEQUENCE: 14
tgggtaatcc atagagccca g                                            21

SEQ ID NO: 15          moltype = DNA  length = 22
FEATURE                Location/Qualifiers
source                 1..22
                       mol_type = other DNA
                       organism = synthetic construct
SEQUENCE: 15
tgggaacctg gaagcttgtc tc                                           22

SEQ ID NO: 16          moltype = DNA  length = 20
FEATURE                Location/Qualifiers
source                 1..20
                       mol_type = other DNA
                       organism = synthetic construct
SEQUENCE: 16
gaattccacg cccagtttga                                              20

SEQ ID NO: 17          moltype = DNA  length = 20
FEATURE                Location/Qualifiers
source                 1..20
                       mol_type = other DNA
                       organism = synthetic construct
SEQUENCE: 17
tggcgtagca ggaagtctga                                              20

SEQ ID NO: 18          moltype = DNA  length = 22
FEATURE                Location/Qualifiers
source                 1..22
                       mol_type = other DNA
                       organism = synthetic construct
SEQUENCE: 18
tgcctccatt gggataaatg tc                                           22
```

SHEEP PDGFD, NUCLEIC ACIDS ENCODING PDGFD AND RECOMBINANT LENTIVIRUS, HOST CELL AND USE THEREOF

CROSS REFERENCE TO RELATED APPLICATION

This patent application claims the benefit and priority of Chinese Patent Application No. 2022106064815 filed with the China National Intellectual Property Administration on May 31, 2022, the disclosure of which is incorporated by reference herein in its entirety as part of the present application.

REFERENCE TO SEQUENCE LISTING

A computer readable XML file entitled "Sequence Listing", that was created on May 6, 2023, with a file size of about 21,179 bytes, contains the sequence listing for this application, has been filed with this application, and is hereby incorporated by reference in its entirety.

TECHNICAL FIELD

The present disclosure belongs to the technical field of molecular cell biology, in particular to sheep PDGFD, nucleic acids encoding PDGFD, and recombinant lentivirus, host cell and use thereof.

BACKGROUND

Mammalian adipose tissue is a complex organ that maintains energy balance under the interaction and synergy of many in vivo factors and in vitro signals. Mature adipose tissues are formed by the gradual differentiation and development of stem cells present in the mesoderm through adipocytes, precursor adipocytes and immature adipocytes. On the one hand, the deposition process of fat in animals is the continuous synthesis and accumulation of fat within mature adipocytes; on the other hand, it is also the continuous proliferation, differentiation and maturation process of precursor adipocytes. Initiating the internal process of precursor adipocytes to adipogenesis activates a series of transcriptional cascade reactions, and promotes the differentiation of precursor adipocytes into mature adipocytes under the synergistic effects of a variety of transcription factors, fatty acid synthetase, internal environment adipokines, metabolic enzymes at all levels, and other related genes and signaling pathways. Therefore, it is particularly important to focus on the molecular regulation of adipogenic differentiation of precursor adipocytes in the study of mammalian fat deposition.

PDGFD gene belongs to the Platelet-derived Growth Factor (PDGF) family, which consists of four members, namely, PDGFA, PDGFB, PDGFC, and PDGFD. PDGF is the main mitogen and strong chemical driver of fibroblasts, smooth muscle cells, and other mesenchymal-derived cells. It involves in the regulation of embryonic development, cell proliferation, cell migration, survival, and chemotaxis by binding to the PDGFR receptor. Sheep PDGFD gene is located on chromosome 15, with a full length of about 28.6 kb and a protein molecular weight of about 43 kDa. It contains two domains, CUB and PDGF. When the PDGFD protein is activated, the CUB domain is hydrolyzed and dissociated to exert the PDGF domain biological activity. To date, there is no study about the functional effect of PDGF domain of sheep PDGFD gene on the differentiation of precursor adipocytes.

SUMMARY

An objective of the present disclosure is to provide a sheep PDGFD, a nucleic acid encoding the PDGFD, and a recombinant lentivirus, a host cell and use thereof.

To achieve the above objective, the present disclosure adopts the following technical scheme.

The present disclosure provides a sheep platelet-derived growth factor PDGFD, which includes one or two of PDGFD-T1 and PDGFD-T2;

the amino acid sequence of PDGFD-T1 is set forth in SEQ ID NO:1, and the amino acid sequence of PDGFD-T2 is set forth in SEQ ID NO:2.

The present disclosure also provides a nucleic acid encoding the sheep platelet-derived growth factor PDGFD, the nucleotide sequences of the nucleic acid are set forth in SEQ ID NOs: 3-4.

The present disclosure also provides a lentivirus expression vector containing the above nucleic acid.

The present disclosure also provides a recombinant lentivirus containing the above lentivirus expression vector.

The present disclosure also provides a host cell containing the above nucleic acid, the lentivirus expression vector, or the recombinant lentivirus.

The present disclosure also provides a product for inhibiting animal fat deposition, wherein the active ingredient of the product is one or more selected from the group consisting of the sheep PDGFD, nucleic acid, lentivirus expression vector, recombinant lentivirus and host cell.

The present disclosure also provides use of the sheep platelet-derived growth factor PDGFD, nucleic acid, lentivirus expression vector, recombinant lentivirus or host cell in the preparation of products for inhibiting animal fat deposition. The present disclosure also includes a method for inhibiting animal fat deposition by administering the product to a sheep in need.

In some embodiments, the product inhibits the differentiation and maturation of precursor adipocytes.

The present disclosure also provides use of the sheep platelet-derived growth factor PDGFD, the nucleic acids, the lentivirus expression vector, the recombinant lentivirus or the host cell in the preparation of CEBPα inhibitor, PPARγ inhibitor, FAS inhibitor, FABP4 inhibitor or LPL inhibitor.

The present disclosure also provides use of the sheep platelet-derived growth factor PDGFD, nucleic acid, lentivirus expression vector, recombinant lentivirus or host cell in the preparation of a product for improving animal meat quality.

Beneficial Effects of the Present Disclosure the present disclosure provides the sheep platelet-derived growth factor PDGFD: PDGFD-T1 and PDGFD-T2. PDGFD-T1 and PDGFD-T2 are able to significantly inhibit the differentiation and maturation of precursor adipocytes and significantly reduce the mRNA relative expression levels of adipogenic differentiation-related genes such as CEBPα, PPARγ, FAS, FABP4 and LPL, thereby inhibiting animal fat deposition and improving animal meat quality, and have important guiding significance in the fields of life science, medical science, animal husbandry and the like.

DETAILED DESCRIPTION OF THE EMBODIMENTS

Figure 1:
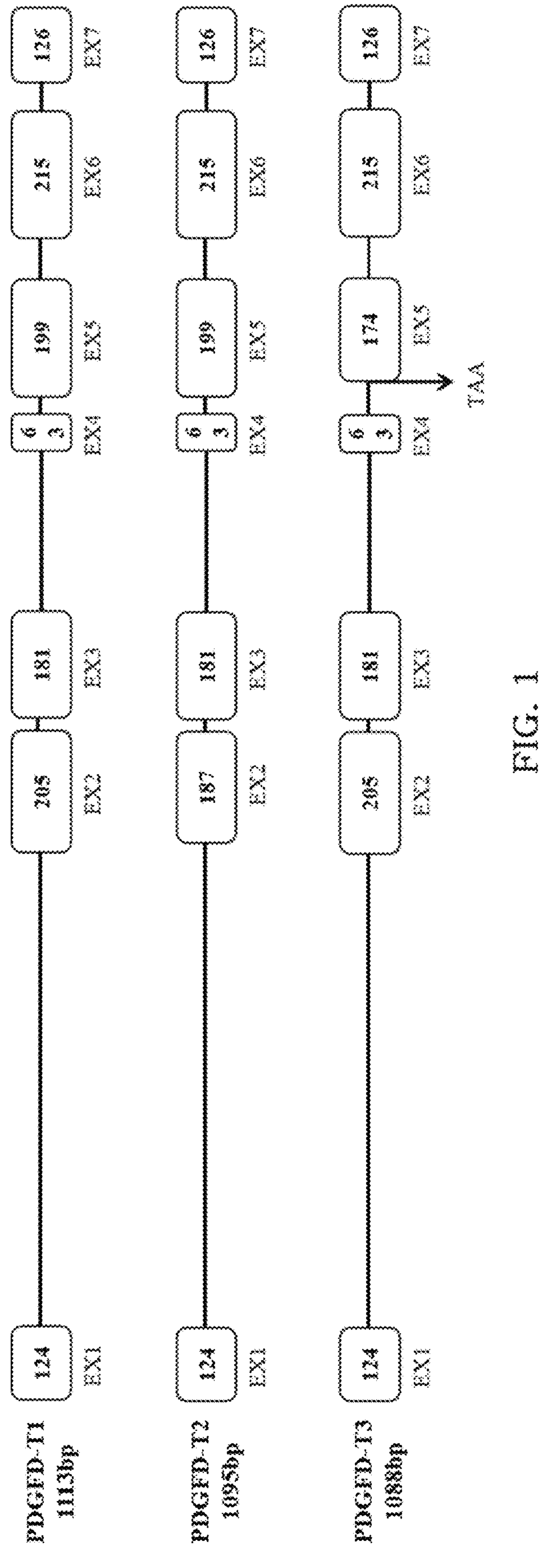
FIG. 1 is a schematic diagram showing the amplification of coding sequences of sheep PDGFD-T1, PDGFD-T2 and PDGFD-T3 genes.

The sheep PDGFD gene is taken as a research object in the present disclosure, and three forms of coding sequences of the PDGFD gene are provided, wherein, PDGFD-T1 and PDGFD-T2 comprise two domains of CUB and PDGF, and PDGFD-T3 has no PDGF domain but retains only the CUB domain. During the functional verification of PDGFD-T1, PDGFD-T2 and PDGFD-T3, it is found that PDGFD-T1 and PDGFD-T2 involve in the inhibition of differentiation of the precursor adipocyte 3T3-L1 into mature adipocytes and the formation of mature lipid droplet, and PDGFD-T3 removes the inhibition effect on the differentiation and maturation of the precursor adipocyte 3T3-L1 after the deletion of PDGF domain.

Based on the above, the present disclosure provides the sheep platelet-derived growth factor PDGFD, which comprises one or two of PDGFD-T1 and PDGFD-T2.

The amino acid sequence of PDGFD-T1 is set forth in SEQ ID NO:1, and the amino acid sequence of PDGFD-T2 is set forth in SEQ ID NO:2.

In some embodiments, PDGFD-T1 encodes 370 amino acids; PDGFD-T2 is encoded with an initial deletion of 18 bp in exon 2 as compared to PDGFD-T1, and encodes 364 amino acids.

The present disclosure also provides a nucleic acid encoding the platelet-derived growth factor PDGFD, and the nucleotide sequences of the nucleic acids are set forth in SEQ ID NOs: 3-4.

The present disclosure also provides a lentivirus expression vector containing the nucleic acids.

In some embodiments, the lentivirus expression vector is preferably pLEX-MCS.

The present disclosure also provides a recombinant lentivirus containing the lentivirus expression vector.

In some embodiments, the recombinant lentivirus is prepared by co-transfecting the lentivirus expression vector and the packaging plasmid into mammalian cells. The mammalian cells are preferably HEK-293T cells. The lentivirus packaging plasmid is preferably psPAX2 and pMD2.G. The transfection method is preferably calcium phosphate transfection. The mass ratio of the lentivirus expression vector, pSPAX2, and pMD2.G is preferably 20:15:6.

The present disclosure also provides the host cell comprising the above nucleic acids, lentivirus expression vector or recombinant lentivirus.

In some embodiments, the host cell is preferably a precursor adipocyte 3T3-L1. According to the technical scheme of the present disclosure, after PDGFD-T1, PDGFD-T2 or PDGFD-T3 lentivirus expression vectors are transfected into the precursor adipocyte 3T3-L1, overexpression can be achieved successfully.

The present disclosure also provides a product for inhibiting animal fat deposition, wherein the active ingredient of the product is one or more selected from the group consisting of the sheep platelet-derived growth factor PDGFD, nucleic acid, lentivirus expression vector, recombinant lentivirus and host cell.

The present disclosure also provides use of the sheep platelet-derived growth factor PDGFD, nucleic acid, lentivirus expression vector, recombinant lentivirus or host cell in the preparation of products for inhibiting animal fat deposition.

In some embodiments the product comprises a reagent or a drug. The product further comprises a pharmaceutically acceptable carrier. As a preferred embodiment, the present disclosure provides use of the above sheep platelet derived growth factor PDGFD, nucleic acids, lentivirus expression vector, recombinant lentiviruses or host cells in the preparation of products for inhibiting the differentiation and maturation of precursor adipocytes.

The present disclosure also provides use of the sheep platelet-derived growth factor PDGFD, the nucleic acids, the lentivirus expression vector, the recombinant lentivirus or the host cell in the preparation of CEBPα inhibitor, PPARγ inhibitor, FAS inhibitor, FABP4 inhibitor or LPL inhibitor.

In some embodiments, PDGFD-T1 and PDGFD-T2 are able to significantly reduce the mRNA relative expression levels of adipogenic differentiation-related genes CEBPα, PPARγ, FAS, FABP4 and LPL. Among them, compared with PDGFD-T1, PDGFD-T2 significantly reduced the relative expression levels of adipogenic differentiation-related genes.

The present disclosure also provides use of the sheep platelet-derived growth factor PDGFD, nucleic acids, lentivirus expression vector, recombinant lentivirus or host cell in the preparation of products for improving animal meat quality.

In some embodiments, PDGFD-T1 and PDGFD-T2 are able to significantly inhibit the differentiation and maturation of precursor adipocytes and significantly reduce the mRNA relative expression levels of adipogenic differentiation-related genes CEBPα, PPARγ, FAS, FABP4 and LPL, thereby inhibiting animal fat deposition, improving animal meat quality and raising lean meat percentage.

In some embodiments, unless otherwise specified, all of the raw material components are commercially available and well known to those skilled in the art.

The technical schemes provided by the present disclosure will be described in detail below with reference to examples. Obviously, the described embodiments are only a partial embodiment of the present disclosure and not all of the embodiments. Based on the embodiments of the present disclosure, all other embodiments obtained by a person of skilled in the art without creative work are within the scope of the present disclosure.

Example 1

1. Construction of Sheep PDGFD Lentivirus Expression Vector 1.1 Sequence Amplification of PDGFD Coding Region With reference to the sequence information of sheep PDGFD transcript XM_004015965.5 in NCBI, the distribution of restriction enzyme sites in the PDGFD coding region was analyzed by BioEdit software, and BamH I and Xho I were selected as restriction enzyme sites for the construction of the expression vector according to the pLEX MCS vector map. Primers for amplifying PDGFD gene coding region sequences were designed by using Primer premier 5.0 software, and protective bases, enzyme cleavage sites, KOZAK sequences and HA tag sequences (Table 1) were added at the 5' end of the primers, and the PDGFD gene coding region sequences (Table 2) were amplified by PCR using sheep fat cDNA as a template.

TABLE 1

Primers for amplifying PDGFD gene coding region sequences

| Primer name | Sequences (5'->3') | Target fragment size |
|---|---|---|
| CDS-PDGFD-F | **cgGGATCC***GCCACC*ATGCACCGGCTCATCCTTGTCTAC (As shown in SEQ ID NO: 5) | 1113 bp |
| CDS-PDGFD-R | **ccCTCGAG**TTAAGCGTAGTCTGGGACGTCGTATGGGTATCGAGGTGGTCTTGAGCTGC (As shown in SEQ ID NO: 6) | |

Note: The bold letters in lowercase represent protective bases, the bold letters in uppercase represent restriction enzyme sites (F: BamH I, R: Xho I), the italicized letters represent KOZAK sequences, and the underlined letters represent HA tag sequences.

TABLE 2

PCR reaction system

| Reagent | Usage |
|---|---|
| PrimeSTAR Max Premix | 5 μL |
| Upstream primer | 0.3 μL |
| Downstream primer | 0.3 μL |
| cDNA | ≤100 ng |
| $ddH_2O$ | Up to 10 μL |

The PCR amplification procedure was as follows: 98° C. for 10 s, 55.5° C. for 5 s and 72° C. for 5 s/kb, 33 cycles in total.

1.2 Construction of Recombinant Eukaryotic Expression Plasmid PLEX-PDGFD (1) The PCR product of the target fragment and the pLEX-MCS vector were subjected to double digestion with restriction endonuclease BamH I-HF (purchased from NEB #R3136) and Xho I (purchased from NEB #R0146). The reaction system is shown in Table 3.

TABLE 3 double digestion reaction system of target fragment and pLEX-MCS vector

| Reagent | pLEX MCS vector | Target fragment |
|---|---|---|
| DNA | 1 μg | 1 μg |
| BamH I-HF | 1 μL | 1 μL |
| Xho I | 1 μL | 1 μL |
| 10 × NEB CutSmart Buffer | 5 μL | 5 μL |
| $ddH_2O$ | Up to 50 μL | Up to 50 μL |

(2) After the digested product was recovered and purified, the digested target fragment was ligated to the pLEX-MCS vector also digested according to the instruction of T4 DNA ligase kit (NEB #M0202S). The reaction system is shown in Table 4.

TABLE 4

PDGFD gene expression vector linkage system

| Reagent | Usage |
|---|---|
| pLEX-MCS vector | 50 ng |
| Target fragment | The molar ratio to vector DNA is about 3 |
| T4 DNA ligase | 1 μL |
| 10 × T4 DNA Buffer | 1 μL |
| $ddH_2O$ | Up to 10 μL |

(3) After the target fragment was ligated to the vector, transformation and monoclonal screening were performed, the recombinant plasmid with correct sequencing and without base mutation was extracted according to the QIAGEN Midi kit instructions, the concentration and purity of the extracted plasmid were determined by using the Nanodrop One nucleic acid quantitator, and the extracted plasmid was stored at −20° C. for later use.

2. Prediction and Analysis of Amplification Sequence Domain in Sheep PDGFD Gene Coding Region (1) The obtained recombinant plasmid was sequenced, and the results show that the recombinant plasmid PDGFD had three forms of coding sequences (see FIG. 1), which were (i) the coding sequence with a full length of 1113 bp by PCR amplification, encoding 370 amino acids, and subsequently named PDGFD-T1; (ii) the coding sequence with a full length of 1095 bp by PCR amplification, encoding 364 amino acids, with a deletion of 18 bp from exon 2 as compared to (i), and subsequently named PDGFD-T2; (iii) the coding sequence with a full length of 1088 bp by PCR amplification, with a deletion of 25 bp from exon 5 as compared to (i), resulting in the early appearance of stop codon TAA, encoding 191 amino acids, and subsequently named PDGFD-T3. The amplification diagram of the coding sequence of sheep PDGFD gene is shown in FIG. 1.

Specifically, the amino acid sequence of PDGFD-T1 was as follows (as shown in SEQ ID NO:1):

```
MHRLILVYTLVCANFCSYRDTSATPQSASIKALRNANLRRDESNHLTDL
YRRDETIQVTGHGHVQSPRFPNSYPRNLLLTWRLHSQEKTRIQLAFDNQ
FGLEEAENDICRYDFVEVEDISETSTVIRGRWCGHKEVPPRITSRTNQI
KITFKSDDYFVAKPGFKIYYSFVEDFQPAAASETNWESVTSSISGVSYH
SPSVTDPTLTADALDKTIAEFDTVEELLKHFNPESWQDDLENLYLDTPH
HRGRSYHDRKSKVDLDRLNDDVKRYSCTPRNYSVNLREELKLTNVVFFP
RCLLVQRCGGNCGCGTVNWKSCACNSGKTVKKYHEVLKFEPGHFKRRGR
AKHMALVDIQLDHHERCDCICSSRPPR.
```

The nucleotide sequence of PDGFD-T1 coding region is as follows (as shown in SEQ ID NO:3):

ATGCACCGGCTCATCCTTGTCTACACGCTAGTCTGCGCAAACTTTTGCAGCTACC
GGGACACCTCTGCCACCCCGCAGAGCGCATCTATCAAAGCTTTGCGTAACGCCAACCTC
AGGCGAGATGAGAGCAATCACCTCACAGACTTGTACCGAAGAGACGAGACCATCCAGG
TGACAGGACACGGCCACGTGCAGAGTCCCCGCTTCCCAAACAGCTACCCTCGCAACCT
GCTTCTGACCTGGCGGCTCCACTCCCAGGAGAAAACAAGGATACAGCTAGCCTTTGACA
ATCAGTTTGGATTAGAGGAAGCGGAAAATGATATCTGTAGGTATGATTTTGTAGAAGTTG
AAGACATATCTGAAACCAGTACTGTTATTAGAGGACGATGGTGTGGACACAAGGAAGTT
CCTCCAAGGATAACATCAAGAACAAACCAGATTAAAATAACGTTCAAGTCTGATGACTA
CTTTGTGGCTAAACCTGGATTCAAGATTTATTATTCTTTTGTGGAAGATTTCCAACCTGCA
GCAGCCTCAGAGACCAACTGGGAGTCAGTCACAAGCTCTATCTCAGGGGTATCCTATCA
CTCTCCATCAGTAACGGACCCCACTCTCACTGCGGATGCTCTGGACAAAACGATTGCAG
AATTTGATACTGTGGAAGAGCTGCTCAAGCACTTCAATCCCGAATCATGGCAAGACGAT
CTTGAGAATCTGTATTTGGATACCCCTCATCATCGAGGCAGATCGTATCATGACAGGAAG
TCAAAAGTTGACCTGGACAGGCTCAACGATGATGTCAAGCGTTACAGTTGCACTCCCAG
GAATTACTCCGTCAACTTGAGAGAAGAGCTGAAGCTTACCAATGTGGTCTTCTTTCCAC
GCTGCCTCCTTGTGCAGCGCTGCGGAGGAAACTGTGGCTGTGGAACTGTCAACTGGAA
GTCCTGTGCGTGCAATTCAGGGAAAACTGTGAAAAAGTATCACGAGGTGTTAAAGTTTG
AACCTGGCCATTTCAAGAGGAGGGGCAGAGCGAAGCACATGGCTCTCGTTGACATCCA
GTTGGATCATCATGAGCGGTGCGACTGTATCTGCAGCTCAAGACCACCTCGATAA.

The amino acid sequence of PDGFD-T2 is follows (as shown in SEQ ID NO: 2):

MHRLILVYTLVCANFCSYRDTSATPQSASIKALRNANLRRDDLYRRDETIQVTGHG
HVQSPRFPNSYPRNLLLTWRLHSQEKTRIQLAFDNQFGLEEAENDICRYDFVEVEDISETST
VIRGRWCGHKEVPPRITSRTNQIKITFKSDDYFVAKPGFKIYYSFVEDFQPAAASETNWESVT
SSISGVSYHSPSVTDPTLTADALDKTIAEFDTVEELLKHFNPESWQDDLENLYLDTPHHRGR
SYHDRKSKVDLDRLNDDVKRYSCTPRNYSVNLREELKLTNVVFFPRCLLVQRCGGNCGCG
TVNWKSCACNSGKTVKKYHEVLKFEPGHFKRRGRAKHMALVDIQLDHHERCDCICSSRPPR.

The nucleotide sequence of PDGFD-T2 coding region is as follows (as shown in SEQ ID NO:4):

ATGCACCGGCTCATCCTTGTCTACACGCTAGTCTGCGCAAACTTTTGCA
GCTACCGGGACACCTCTGCCACCCCGCAGAGCGCATCTATCAAAGCTTT
GCGTAACGCCAACCTCAGGCGAGATGACTTGTACCGAAGAGACGAGACC
ATCCAGGTGACAGGACACGGCCACGTGCAGAGTCCCCGCTTCCCAAACA
GCTACCCTCGCAACCTGCTTCTGACCTGGCGGCTCCACTCCCAGGAGAA
AACAAGGATACAGCTAGCCTTTGACAATCAGTTTGGATTAGAGGAAGCG
GAAAATGATATCTGTAGGTATGATTTTGTAGAAGTTGAAGACATATCTG
AAACCAGTACTGTTATTAGAGGACGATGGTGTGGACACAAGGAAGTTCC
TCCAAGGATAACATCAAGAACAAACCAGATTAAAATAACGTTCAAGTCT
GATGACTACTTTGTGGCTAAACCTGGATTCAAGATTTATTATTCTTTTG
TGGAAGATTTCCAACCTGCAGCAGCCTCAGAGACCAACTGGGAGTCAGT
CACAAGCTCTATCTCAGGGGTATCCTATCACTCTCCATCAGTAACGGAC

-continued

CCCACTCTCACTGCGGATGCTCTGGACAAAACGATTGCAGAATTTGATA
CTGTGGAAGAGCTGCTCAAGCACTTCAATCCCGAATCATGGCAAGACGA
TCTTGAGAATCTGTATTTGGATACCCCTCATCATCGAGGCAGATCGTAT
CATGACAGGAAGTCAAAAGTTGACCTGGACAGGCTCAACGATGATGTCA
AGCGTTACAGTTGCACTCCCAGGAATTACTCCGTCAACTTGAGAGAAGA
GCTGAAGCTTACCAATGTGGTCTTCTTTCCACGCTGCCTCCTTGTGCAG
CGCTGCGGAGGAAACTGTGGCTGTGGAACTGTCAACTGGAAGTCCTGTG
CGTGCAATTCAGGGAAAACTGTGAAAAAGTATCACGAGGTGTTAAAGTT
TGAACCTGGCCATTTCAAGAGGAGGGGCAGAGCGAAGCACATGGCTCTC
GTTGACATCCAGTTGGATCATCATGAGCGGTGCGACTGTATCTGCAGCT
CAAGACCACCTCGATAA.

The amino acid sequence of PDGFD-T3 is as follows (as shown in SEQ ID NO:7):

MHRLILVYTLVCANFCSYRDTSATPQSASIKALRNANLRRDESNHLTDLY

RRDETIQVTGHGHVQSPRFPNSYPRNLLLTWRLHSQEKTRIQLAFDNQFG

LEEAENDICRYDFVEVEDISETSTVIRGRWCGHKEVPPRITSRTNQIKIT

FKSDDYFVAKPGFKIYYSFVEDFQPAAASETNWESVTSSIS.

The nucleotide sequence of PDGFD-T3 coding region is as follows (as shown in SEQ ID NO:8):

ATGCACCGGCTCATCCTTGTCTACACGCTAGTCTGCGCAAACTTTTGCAG

CTACCGGGACACCTCTGCCACCCCGCAGAGCGCATCTATCAAAGCTTTGC

GTAACGCCAACCTCAGGCGAGATGAGAGCAATCACCTCACAGACTTGTAC

CGAAGAGACGAGACCATCCAGGTGACAGGACACGGCCACGTGCAGAGTCC

CCGCTTCCCAAACAGCTACCCTCGCAACCTGCTTCTGACCTGGCGGCTCC

ACTCCCAGGAGAAAACAAGGATACAGCTAGCCTTTGACAATCAGTTTGGA

TTAGAGGAAGCGGAAAATGATATCTGTAGGTATGATTTTGTAGAAGTTGA

AGACATATCTGAAACCAGTACTGTTATTAGAGGACGATGGTGTGGACACA

AGGAAGTTCCTCCAAGGATAACATCAAGAACAAACCAGATTAAAATAACG

TTCAAGTCTGATGACTACTTTGTGGCTAAACCTGGATTCAAGATTTATTA

TTCTTTTGTGGAAGATTTCCAACCTGCAGCAGCCTCAGAGACCAACTGGG

AGTCAGTCACAAGCTCTATCTCATAACGGACCCCACTCTCACTGCGGATG

CTCTGGACAAAACGATTGCAGAATTTGATACTGTGGAAGAGCTGCTCAAG

CACTTCAATCCCGAATCATGGCAAGACGATCTTGAGAATCTGTATTTGGA

TACCCCTCATCATCGAGGCAGATCGTATCATGACAGGAAGTCAAAAGTTG

ACCTGGACAGGCTCAACGATGATGTCAAGCGTTACAGTTGCACTCCCAGG

AATTACTCCGTCAACTTGAGAGAAGAGCTGAAGCTTACCAATGTGGTCTT

CTTTCCACGCTGCCTCCTTGTGCAGCGCTGCGGAGGAAACTGTGGCTGTG

GAACTGTCAACTGGAAGTCCTGTGCGTGCAATTCAGGGAAAACTGTGAAA

AAGTATCACGAGGTGTTAAAGTTTGAACCTGGCCATTTCAAGAGGAGGGG

CAGAGCGAAGCACATGGCTCTCGTTGACATCCAGTTGGATCATCATGAGC

GGTGCGACTGTATCTGCAGCTCAAGACCACCTCGATAA.

(2) The domains of three coding sequences of PDGFD were predicted by using the on-line software SMART (http://smart.embl-heidelberg.de/).

Figure 2:
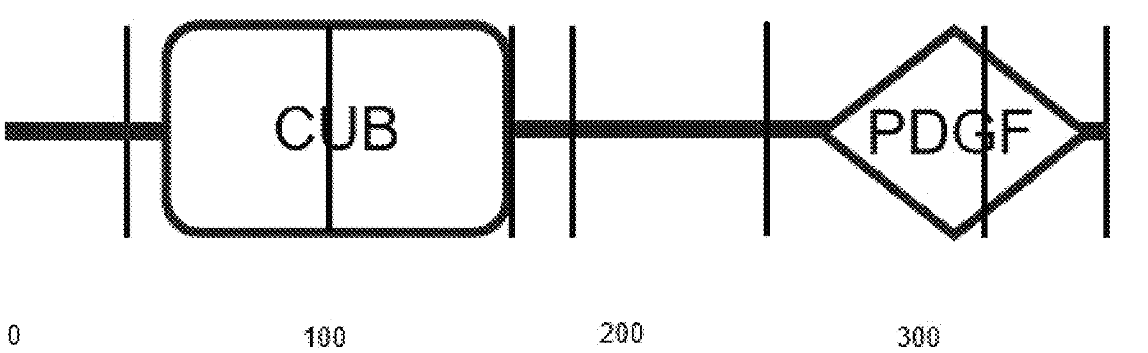
FIG. 2 is a graph showing the prediction results of sheep PDGFD-T1, PDGFD-T2, and PDGFD-T3 domains.
Figure 2:
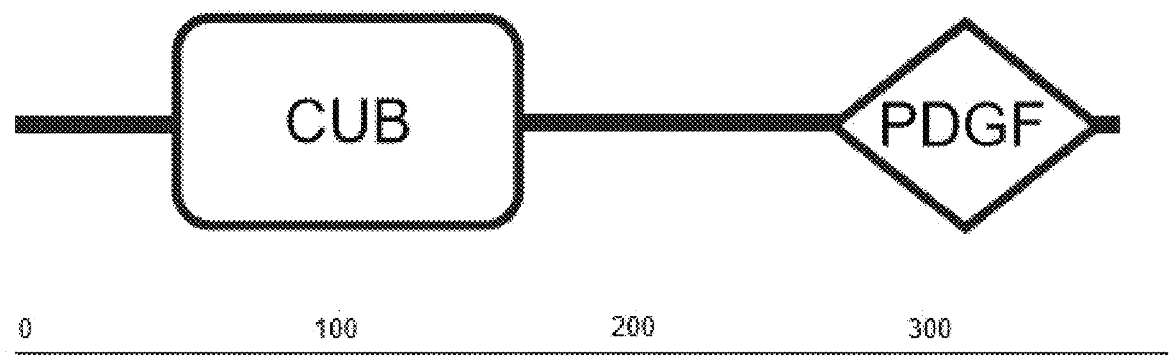
Figure 2:
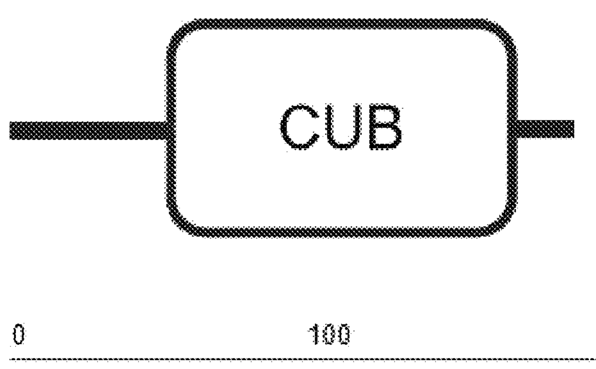

The results showed that sheep PDGFD-T1 and PDGFD-T2 included both CUB and PDGF domains. CUB domain was encoded by exons 2 and 3 of PDGFD gene, and PDGF domain was encoded by exons 6 and 7. However, the PDGF domain was lost in PDGFD-T3, only the CUB domain was retained (see FIG. 2).

3. Packaging of PLEX-PDGFD Recombinant Lentivirus

According to the PLEX-MCS lentivirus packaging instructions, the recombinant lentivirus plasmids PDGFD-T1, PDGFD-T2, PDGFD-T3 and the packaging plasmids (psPAX2 and pMD2.G) were co-transfected into 293T cells by calcium phosphate transfection method for lentivirus packaging. The specific steps were as follows:

(1) 2-2.5×$10^6$ 293T cells were inoculated on a cell culture plate every 10 cm, and the transfected lentivirus plasmid was prepared when the cells were adherent and reached 70-80% growth confluence;

(2) The recombinant lentivirus plasmids and the packaging plasmids (psPAX2 and pMD2.G) were co-transfected into 293T cells by calcium phosphate transfection method for lentivirus packaging. Transfection system (1 mL/10 cm plate) included 20 μg of recombinant lentivirus plasmid, 15 μg of packaging plasmid (psPAX2) and 6 μg of envelope plasmid (pMD2.G); sterile $H_2O$ was used to dilute the resulting plasmid mixture to 500 μL to obtain a diluted solution; 500 μL of 2×HBS(Hepes buffered saline) was added into the diluted solution and mixed completely by rapid vortexing to obtain a mixture.

(3) 50 μL of 2.5 M $CaCl_2$ was added dropwise to the mixture while vortexing. After incubation at room temperature for 20 minutes, the mixture was added to cell culture plates.

(4) Fresh medium was replaced after 12-14 h, and the cells were transferred to a 32° C. incubator after 10 h.

(5) The cell supernatant (i.e., lentivirus infection solution) was collected after 14-16 h and filtered with a 0.45 μm filter. The filtered supernatant could be directly used to infect target cells.

4. Infection of Target Cells with PLEX-PDGFD Recombinant Lentivirus (1) Target cells (precursor adipocyte line 3T3-L1, ATCC® CL-173™) were inoculated in six-well cell plates, and lentivirus was infected when the cells were adherent and reached 60-70% growth confluence.

(2) The cell supernatant containing the lentivirus packaging plasmids and fresh medium (v/v, 1:1) as well as 10 μg/mL polybrene were added to the plates inoculated the target cells. The cells were then placed in an incubator at 32° C.

(3) The cells were transferred to a 37° C. cell incubator after 14-16 h, the fresh medium was replaced after 10 h, and the cells in the fresh medium were continued to be cultured.

(4) After 48 h, the cells were transferred to a 10 cm cell culture plate, and cell culture medium containing 1.5 μg/mL puromycin was added for screening and culture of resistant cells. During the period, the cell culture medium containing 1.5 μg/mL puromycin was replaced every 3-4 d.

5. Detection of PDGFD Overexpression in 3T3-L1 Cell

After the above PDGFD-T1, PDGFD-T2, and PDGFD-T3 lentivirus expression vectors were transfected into the precursor adipocytes 3T3-L1, the overexpression of PDGFD-T1, PDGFD-T2, and PDGFD-T3 in 3T3-L1 cells was detected by using HA tag antibody (purchased from Sigma #H3663) according to the conventional Western Blot experimental method.

Figure 3:
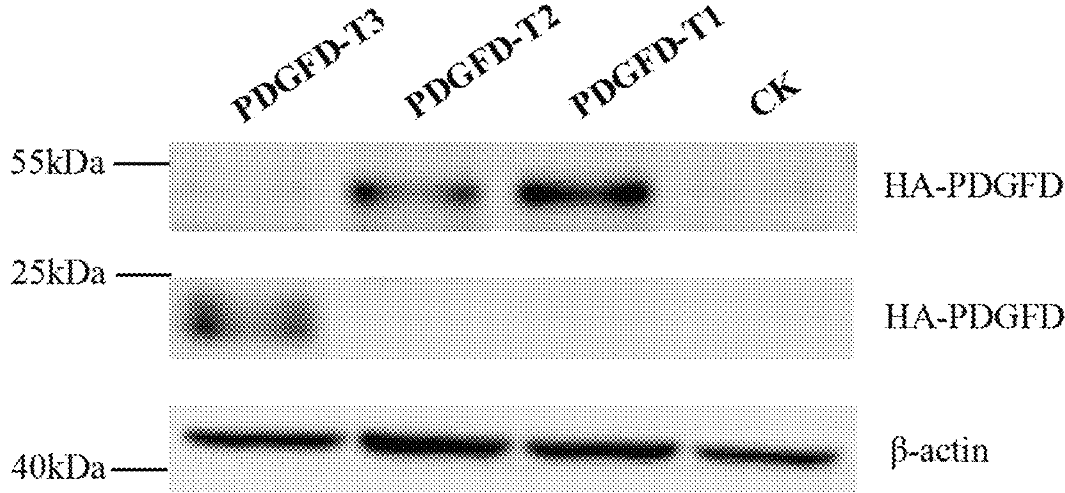
FIG. 3 shows the overexpression of PDGFD-T1, PDGFD-T2 and PDGFD-T3 detected by HA-labeled antibodies in 3T3-L1 cells.

The results showed that PDGFD-T1, PDGFD-T2, and PDGFD-T3 were all overexpressed in 3T3-L1 cells successfully (see FIG. 3). The 3T3-L1 cells overexpressing PDGFD could continue to be used in subsequent experiments.

6. Functional Effect of PDGF Domain of PDGFD Gene on the Adipogenic Differentiation of Precursor Adipocytes 3T3-L1

(1) Induced Differentiation of Precursor Adipocytes and Detection of Oil Red O Staining 3T3-L1 cells overexpressing PDGFD-T1, PDGFD-T2 and PDGFD-T3 and the control group cells were induced to differentiate according to the cell line culture instruction (ATCC® CL-173™), wherein the control group cells were the precursor adipocyte line 3T3-L1 cells without any treatment; after 10 days of induced differentiation, the induced cells were stained according to the oil red O staining solution instruction (purchased from Solarbio, #G1260) to detect the effect of PDGFD on the ability of 3T3-L1 cells to differentiate and mature to form lipid droplets.

Figure 4:
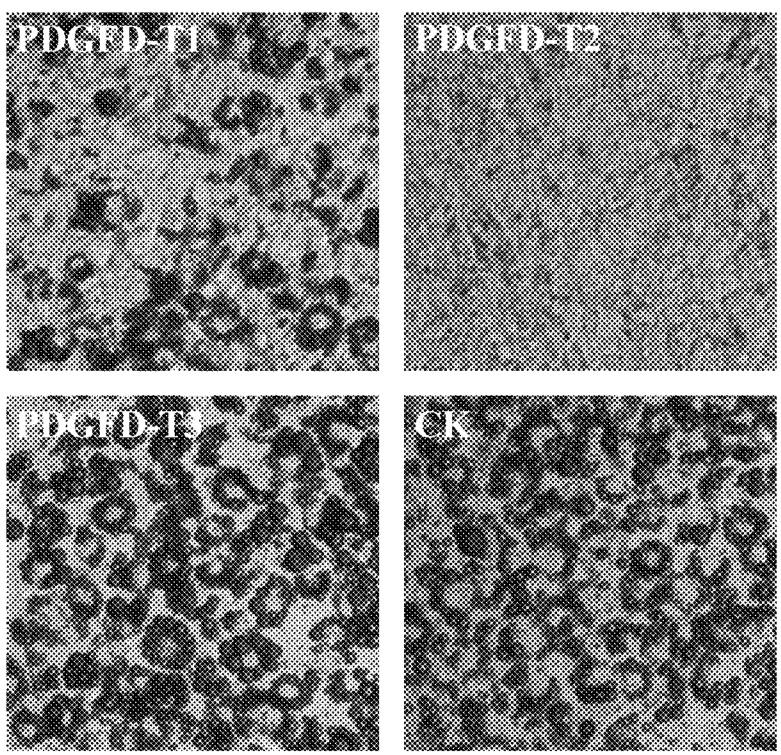
FIG. 4 shows the effect of PDGFD-T1, PDGFD-T2 and PDGFD-T3 groups on the adipogenic differentiation of 3T3-L1 cells detected by oil red O staining.

As shown in FIG. 4, the number of "ring-like" lipid droplets in the PDGFD-T1 group was significantly lower than that in the CK group (control group). The "ring-like" lipid droplets could not be observed in the PDGFD-T2 group. Compared with the CK group, the oil red O staining result in the PDGFD-T3 group lacking the PDFD domain was not significantly different.

Figure 5:
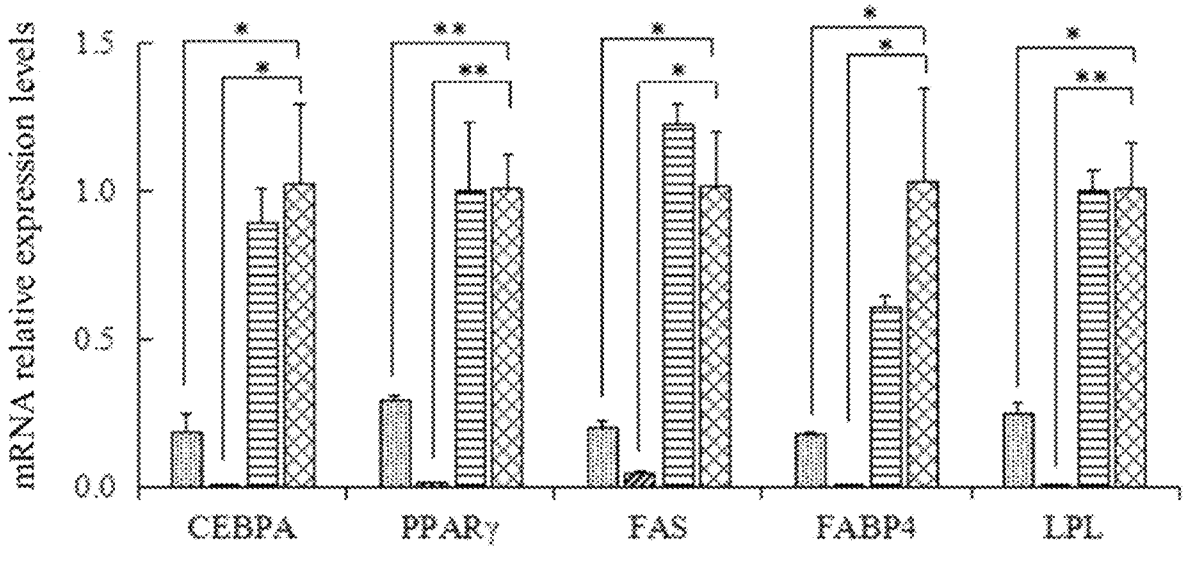
FIG. 5 shows the effects of PDGFD-T1, PDGFD-T2 and PDGFD-T3 on the expression of genes related to adipogenic differentiation in 3T3-L1 cells detected by qRT-PCR.

(2) Detection of Expression of Adipogenic Differentiation Related Genes in 3T3-L1 Cells To further verify the effect of PDGFD on the differentiation and maturation of precursor adipocytes, the expression of adipogenic differentiation related genes in 3T3-L1 cells was detected at the molecular level. RNA was extracted from 3T3-L1 cells that had been induced to differentiate for 10 days, and reversely transcribed into cDNA, which was used as the template for qRT-PCR detection (the primers for qRT-PCR amplification are shown in Table 5). The results show (FIG. 5) that, after 10 days of induction and differentiation, the mRNA relative expression levels of the adipogenic differentiation related genes CEBPα, PPARγ, FAS, FABP4 and LPL in the PDGFD-T1 and PDGFD-T2 groups were all significantly lower than those in the control group CK ($P<0.05$). The mRNA relative expression levels of the adipogenic differentiation related genes CEBPα, PPARγ, FAS, FABP4 and LPL in the PDGFD-T3 group, which lacked the PDFD domain, was not significantly different from those in the control group CK.

TABLE 5 primers for qRT-PCR amplification of adipogenic differentiation related genes

| Primer name | Sequences (5'→3') | Target fragment size |
|---|---|---|
| MqPCR-CEBPA-F | CCAAGAAGTCGGTGGACAAGAA (SEQ ID NO: 9) | 148 bp |
| MqPCR-CEBPA-R | CGGTCATTGTCACTGGTCAAC (SEQ ID NO: 10) | |
| MqPCR-PPARγ-F | GTGCCAGTTTCGATCCGTAGA (SEQ ID NO: 11) | 142 bp |
| MqPCR-PPARγ-R | GGCCAGCATCGTGTAGATGA (SEQ ID NO: 12) | |
| MqPCR-FASN-F | GGAGGTGGTGATAGCCGGTAT (SEQ ID NO: 13) | 140 bp |
| MqPCR-FASN-R | TGGGTAATCCATAGAGCCCAG (SEQ ID NO: 14) | |
| MqPCR-FABP4-F | TGGGAACCTGGAAGCTTGTCTC (SEQ ID NO: 15) | 197 bp |
| MqPCR-FABP4-R | GAATTCCACGCCCAGTTTGA (SEQ ID NO: 16) | |
| MqPCR-LPL-F | TGGCGTAGCAGGAAGTCTGA (SEQ ID NO: 17) | 218 bp |
| MqPCR-LPL-R | TGCCTCCATTGGGATAAATGTC (SEQ ID NO: 18) | |

Based on the above experimental results, PDGFD-T1 and PDGFD-T2 were able to significantly inhibit the differentiation of precursor adipocytes 3T3-L1 into mature adipocytes and the formation of mature lipid droplets; PDGFD-T3 lost its inhibitory effect on the differentiation and maturation of precursor adipocytes 3T3-L1 after the deletion of PDGF domain, indicating that PDGF domain was an important component of PDGFD in inhibiting the differentiation and maturation of precursor adipocytes 3T3-L1.

The above described are only preferred embodiments of the present disclosure, it should be understood by those skilled in the art that, without departing from the principle of the present disclosure, several improvements and modifications can be made, and these improvements and modifications should also fall within the scope of the present disclosure.

What is claimed is:

1. A lentiviral expression vector containing a nucleic acid, wherein the nucleic acid encodes a sheep platelet-derived growth factor D (PDGFD), wherein the PDGFD is PDGFD-T2; and wherein the amino acid sequence of PDGFD-T2 is set forth in SEQ ID NO:2.

2. The lentiviral expression vector of claim 1, wherein the nucleotide sequence of the nucleic acid is set forth in SEQ ID NO: 4.

3. A product for inhibiting animal fat deposition, wherein an active ingredient of the product is one or more selected from the group consisting of a sheep PDGFD, a nucleic acid encoding the sheep PDGFD, a lentivirus expression vector containing the nucleic acid, a recombinant lentivirus containing the lentivirus expression vector, and a host cell containing the nucleic acid;

wherein the PDGFD is PDGFD-T2; and wherein the amino acid sequence of PDGFD-T2 is set forth in SEQ ID NO:2.

4. A method for inhibiting animal fat deposition, comprising administering the product of claim 3 to a sheep in need.

5. The method according to claim 4, wherein the product inhibits the differentiation and maturation of precursor adipocytes.

6. The method according to claim 4, wherein the product is a CEBPα inhibitor, a PPARγ inhibitor, a FAS inhibitor, a FABP4 inhibitor or a LPL inhibitor.

* * * * *